(12) United States Patent
Kang et al.

(10) Patent No.: US 9,079,047 B2
(45) Date of Patent: Jul. 14, 2015

(54) COSMETIC COMPOSITION FOR SKIN WHITENING

(75) Inventors: Hyun Seo Kang, Yongin-si (KR); Seung Hyun Kang, Yongin-si (KR); Ji Hyun Kim, Yongin-si (KR); Yong Joo Na, Yongin-si (KR); Jun Cheol Cho, Yongin-si (KR); Byung Guen Chae, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 166 days.

(21) Appl. No.: 13/398,353

(22) Filed: Feb. 16, 2012

(65) Prior Publication Data

US 2012/0213719 A1 Aug. 23, 2012

(30) Foreign Application Priority Data

Feb. 18, 2011 (KR) ........................ 10-2011-0014441

(51) Int. Cl.
*A61K 36/00* (2006.01)
*A61K 36/575* (2006.01)
*A61K 36/752* (2006.01)
*A61K 36/16* (2006.01)
*A61K 36/355* (2006.01)
*A61Q 19/02* (2006.01)
*A61K 8/97* (2006.01)

(52) U.S. Cl.
CPC . *A61Q 19/02* (2013.01); *A61K 8/97* (2013.01); *A61K 2800/5922* (2013.01)

(58) Field of Classification Search
None
See application file for complete search history.

(56) References Cited

U.S. PATENT DOCUMENTS

| 6,383,525 B1 * | 5/2002 | Hsu et al. ....................... 424/728 |
| 2007/0082024 A1 * | 4/2007 | Matsumoto et al. .......... 424/439 |
| 2011/0189314 A1 * | 8/2011 | Debaun et al. ................ 424/727 |

FOREIGN PATENT DOCUMENTS

| JP | 2008081472 A | * | 4/2008 |
| JP | 2010150217 A | * | 7/2010 |
| KR | 2003071893 A | * | 9/2003 |
| KR | 2004097764 A | * | 11/2004 |
| KR | 2008044612 A | * | 5/2008 |

* cited by examiner

*Primary Examiner* — Qiuwen Mi
(74) *Attorney, Agent, or Firm* — Nixon & Vanderhye P.C.

(57) ABSTRACT

The present invention relates to a cosmetic composition for skin whitening containing at least two selected from the group consisting of a *Magnolia obovata* bark extract, a *Citrus unshiu* peel extract, a wild soybean extract, a *Ginkgo biloba* leaf extract, and a Honeysuckle extract, which composition depresses melanocytes, blocks stimulation from inflammation, UV radiation, or melasma blood vessels, strengthens melanocyte-supporting DEJs, inhibits skin hyper-pigmentation like skin spots and UV-induced skin tanning, and improves the skin tone and complexion look healthy and bright.

15 Claims, No Drawings

COSMETIC COMPOSITION FOR SKIN WHITENING

This application claims priority to Korean Patent Application No. 10-2011-0014441 filed 18 Feb. 2011, the entire contents of which is hereby incorporated by reference.

BACKGROUND OF THE INVENTION

1. Field of the Invention

The present invention relates to a cosmetic composition for skin whitening and, more particularly, to a cosmetic composition for skin whitening that contains at least two selected from the group consisting of a *Magnolia obovata* bark extract, a *Citrus unshiu* peel extract, a wild soybean extract, a *Ginkgo biloba* leaf extract, and a Honeysuckle extract, to improve or prevent skin pigmentation and dark-toned skin and substantially inhibit a production of melamine, thereby providing a whitening effect.

2. Background Art

Human skin color (complexion) and pigmentation such as formation of melasma or skin spots are ascribed to various factors, including the activity of melanin-producing melanocytes, the blood vessel distribution, the skin thickness, and the existence of body pigments such as carotenoids, bilirubin, etc. Among these factors, the primary determinant is a darkening pigment called "melanin", which is produced by the actions of different enzymes in melanocytes. There are three main factors that affect melanin production: genetic factors, physiological factors related to hormone secretion, and environmental factors such as stress, ultraviolet (UV) irradiation, etc.

Melanins that determine the skin complex are produced in melanocytes, where different enzymes such as tyrosinase participate together in polymerization oxidation reaction using amino acid called "tyrosine" existing in the body as a substrate to produce dark brown pigments, melanins. The melanins thus produced migrate towards the epidermal cells called "keratinocytes" along melanocyte dendrites and form a hat-shaped structure around the nuclei in the keratinocytes to play an important role of protecting DNAs from UVR-induced damage and eliminating free radicals, thereby protecting proteins in the cell. There exists no enzyme for decomposition of melanins. Instead, melanins are removed along with dead keratinocytes shed from the skin. An over-production of melanin results in hyper-pigmentation that shows up as melasma, freckles, spots, etc. with an adverse effect in the cosmetic aspect. Such a UVR-induced hyper-pigmentation has become more serious with an increase in the population enjoying the leisure time with outdoor activities and hence posed heavy psychological burdens in the skin cosmetic aspect to prevent a normal social life in the worse cases. For example, Asian women have taken a liking to a fair skin and considered a fair skin as the criteria for beauty, so there has been an increasing desire for prevention and improvement of pigmentary disorders or hyper-pigmentation. Hence, with an increasing need for developing whitening products to prevent an over-production of melanin, many attempts have been made to contrive whitening products, such as, for example, tyrosinase inhibitors (e.g., kojic acid, arbutin, etc), hydroquinone, vitamin A, vitamin C as a representative antioxidant, and their derivatives. These whitening products are, however, limited in their uses due to some problems in regard to skin safety, stability in formulation, and insufficient whitening effect. The conventional whitening products also have much to be desired to meet the latest customers' desires for a fundamental whitening effect, since they because their whitening effect is only temporary and cannot guarantee the skin health in many aspects.

It has been recently reveled that the simple whitening techniques in association with inhibition of melanin production and promotion of melanin secretion cannot offer a fundamental achievement of the whitening effect. As the development of biotechnology discloses that skin pigmentation involves a considerably complicated mechanism, especially noteworthy are bio-scientific whitening researches for imposing a whitening effect on different target paths simultaneously to achieve a more fundamental whitening effect. There have also been arguments that whitening cosmetic products have a stronger whitening effect when applied on several targets rather than on one or two targets. With recent reports that whitening is closely related to ageing, it is getting more persuasive to treat the pigment-related skin problems, such as skin complexion, melasma, or spots, depending on the healthy condition in the skin. Accordingly, studies have been actively made on the approaches for analyzing and managing the microscopic environment surrounding melanocytes to fundamentally improve the problem with the pigmented skin area which is hard to remove of over-produced melanin.

There is little difference in the number of melanocytes in the skin among races, but a considerably greater number of melanins are produced in the skin of black people upon exposure to UV radiation. In other words, the skin color depends on the produced amount of melanins in the melanocytes. In regard to this, a precise analysis on the melanocytes and their microscopic environment has revealed that the production of melanins have a close relation to the five factors: sensitivity of melanocytes, DNA denaturation of melanocytes, stimulation of inflammation substances on melanocytes, melasma blood vessels around melanocytes, and melanocyte-supporting DEJ (Dermal-Epidermal Junction) collagen fibers. With a problem related to the five factors, the skin sensitively responds to the stimulation from the external harmful environment to produce more melanins, which then migrate downwards in a part of the skin and become difficult to remove from the skin.

The problem with the five factors includes, for example, over-production of melanin in melanocytes under weak stimulation; increase of stimulus induced by inflammation; readiness of DNA denaturation of melanocytes; readiness of production of melasma blood vessels; or deteriorated elasticity of melanocyte-supporting DEJ. Such an unhealthy condition of melanocytes and their environments causes over-production of melanins under weak stimulation, making melanins difficult to remove from the skin and resulting in pigment-related skin problems such as skin spots and dark-toned skin. There is hence a pressing demand for studies on an approach to fundamentally make the ecosystem of the melanins in the skin healthy.

SUMMARY OF THE INVENTION

Through the recent bio-scientific research trends and intensive studies on melanocytes and their microscopic environment, the inventors of the present invention have found it out that ageing is closely related to whitening so that the skin tends to have an unhealthy complexion with ageing. The inventors also revealed that a remarkable whitening effect can be attained using a composition containing a mixture of a *Magnolia obovata* bark extract having a melanocyte-depressant effect, a *Citrus unshiu* peel extract excellent in neutralizing inflammation substances, a wild soybean extract for preventing DNA denaturation, a *Ginkgo biloba* leaf extract for inhibiting a production of melasma blood vessels, and a Honeysuckle extract for accelerating synthesis of DEJ elastic fibers.

It is therefore an object of the present invention to provide a cosmetic composition for skin whitening designed to substantially reduce the production of melanins and make the removal of melanins easier, thereby providing an ultimately remarkable whitening effect and improving or preventing hyper-pigmentation and dark-toned skin, on the basis of the conception that the appearance of the skin concealing melanins inside is greatly dependent upon the healthy conditions of melanocytes and their microscopic environment.

To accomplish the above object, the present invention provides a cosmetic composition comprising, as active ingredients, at least two selected from the group consisting of a *Magnolia obovata* bark extract, a *Citrus unshiu* peel extract, a wild soybean extract, a *Ginkgo biloba* leaf extract, and a Honeysuckle extract.

The cosmetic composition of the present invention contains a mixture of a *Magnolia obovata* bark extract, a *Citrus unshiu* peel extract, a wild soybean extract, a *Ginkgo biloba* leaf extract, and a Honeysuckle extract to substantially make the melanin-related ecosystem inside the skin healthier and thus improve hyper-pigmentation and dark-toned skin, thereby providing an excellent whitening effect as well as a skin safety.

DETAILED DESCRIPTION OF THE PREFERRED EMBODIMENT

The cosmetic composition for skin whitening according to the present invention comprises, as active ingredients, at least two selected from the group consisting of a *Magnolia obovata* bark extract, a *Citrus unshiu* peel extract, a wild soybean extract, a *Ginkgo biloba* leaf extract, and a Honeysuckle extract.

Hereinafter, the present invention will be described in further detail.

The *Magnolia obovata* bark extract used as an active ingredient of the present invention is taken from a deciduous tree native to Japan (in the *Magnolia* family of *Ranunculus japonicus* Thunb.). In the herbal medicine, the *magnolia obovata* bark has been utilized for treating various diseases like stomach ache, asthma, and so forth. This bark extract is believed to contain a great content of compounds such as machilol, magnolol and honokiol. A treatment with the *Magnolia obovata* bark extract on melanocytes results in an excellent effect of depressing the active melanocytes to minimize the activity of producing melanins. In other words, the *Magnolia obovata* bark extract inhibits the melanin production process induced by an external stimulus and helps providing a healthy and clean environment of the skin cells inside the skin.

The *Magnolia obovata* bark extract used as an active ingredient in the present invention is extracted from the bark of a *Magnolia* tree according to a traditional extraction and separation method. Preferably, the *Magnolia obovata* bark washed with clean water is soaked in a solvent containing 70% purified water and 30% alcohol at 25° C. for 6 hours to extract active ingredients. After extraction, the solution is subjected to one filtration with a 3 μm-pore filter and one filtration with a 1 μm-pore filter to eliminate foreign materials and then one filtration with a sterile filter to eliminate microorganisms to yield a *Magnolia obovata* bark extract.

As contrived on the basis of the idea that *citrus* fruits contain four times more vitamin C in their peel than in their flesh, the *Citrus unshiu* peel extract used as an active ingredient of the present invention is known to have a great content of bioflavonoids. A latest research on the whitening dermatology has reported that the representative inflammation substance, IL-8 (Interleukin-8), stimulates melanocytes to accelerate a production of melanins. A treatment with the *Citrus unshiu* peel extract on melanocytes demonstrates that the *Citrus unshiu* peel extract has an excellent effect of neutralizing the inflammation substance, IL-8. In other words, this peel extract neutralizes the substance stimulating the melanocytes to inhibit a production of melanins and substantially helps making the skin healthy and clean.

The *Citrus unshiu* peel extract used as an active ingredient in the present invention is extracted from the peel of *citrus* fruits according to a traditional extraction and separation method. Preferably, the *Citrus unshiu* peel washed with clean water is soaked in a solvent containing 70% purified water and 30% alcohol at 25° C. for 6 hours to extract active ingredients. After extraction, the solution is subjected to one filtration with a 3 μm-pore filter and one filtration with a 1 μm-pore filter to eliminate foreign materials and then one filtration with a sterile filter to eliminate microorganisms to yield a *Citrus unshiu* peel extract.

The wild soybean extract used as an active ingredient of the present invention is known to have a good antioxidant effect and a good UV screening effect. Like other cells, melanocytes under UV radiations are susceptible to DNA denaturation to produce a thymine dimmer as one of DNA mutants. A treatment with the wild soybean extract of the present invention on melanocytes results in a concentration-dependent reduction of UV-induced DNA denaturation of the melanocytes. As the cells under DNA denaturation cannot do its normal functions, melanocytes under DNA denaturation is ready to over-produce melanins. The wild soybean extract inhibits the DNA denaturation of melanocytes to help making the skin healthy and clean.

The wild soybean extract used as an active ingredient in the present invention is extracted from wild soybeans according to a traditional extraction and separation method. Preferably, the wild soybeans washed with clean water are soaked in a solvent containing 70% purified water and 30% alcohol at 25° C. for 6 hours to extract active ingredients. After extraction, the solution is subjected to one filtration with a 3 μm-pore filter and one filtration with a 1 μm-pore filter to eliminate foreign materials and then one filtration with a sterile filter to eliminate microorganisms to yield a wild soybean extract.

The *Ginkgo biloba* leaf extract used as an active ingredient of the present invention contains a large amount of bioflanonoids like quercetin, kaempferol, and isohamnetin. The most mature green leaves taken in September or October before falling off are believed to have the most effective ingredients. The *Ginkgo biloba* leaf extract inhibits generation of melasma blood vessels predominantly found in the melasma areas to prevent abnormal activation of melanocytes. A treatment with the *Ginkgo biloba* leaf extract shows that there is almost little increase in the melasma blood vessels produced under UV radiation, while an exposure to UVB (50 mJ) normally results in an increase of the melasma blood vessels by about 2.5 times. Such an inhibition of the production of melasma blood vessels reduces the activity of melanocytes and substantially decreases the ability of producing melanins, thereby achieving a whitening effect to lighten the skin tone.

The *Ginkgo biloba* leaf extract used as an active ingredient in the present invention is extracted from *Ginkgo biloba* leaves according to a traditional extraction and separation method. Preferably, the *Ginkgo biloba* leaves washed with clean water are soaked in a solvent containing 70% purified water and 30% alcohol at 25° C. for 6 hours to extract active ingredients. After extraction, the solution is subjected to one filtration with a 3 μm-pore filter and one filtration with a 1 μm-pore filter to eliminate foreign materials and then one filtration with a sterile filter to eliminate microorganisms to yield a Ginkgo biloba leaf extract.

The Honeysuckle extract used as an active ingredient of the present invention is also referred to as "gold and silver flower extract" because Honeysuckle has gold and silver flowers in pairs. This flower extract promotes synthesis of elastic fibers in DEJ (Dermal-Epidermal Junction) to make the melanocyte-supporting layer elastic. With the weak DEJ, melanins produced from the melanocytes tend to migrate into the dermis and become difficult to eliminate from the skin. The Honeysuckle extract prevents melanins from being difficult to remove and makes it easier to eliminate melanins from the skin. In other words, this extract increases the elasticity of the skin and also helps a rapid recovery of the skin tone light and healthy.

The Honeysuckle extract used as an active ingredient in the present invention is extracted from Honeysuckle leaves or stems according to a traditional extraction and separation method. Preferably, the Honeysuckle leaves or stems washed with clean water are soaked in a solvent containing 70% purified water and 30% alcohol at 25° C. for 6 hours to extract active ingredients. After extraction, the solution is subjected to one filtration with a 3 μm-pore filter and one filtration with a 1 μm-pore filter to eliminate foreign materials and then one filtration with a sterile filter to eliminate microorganisms to yield a Honeysuckle extract.

The cosmetic composition of the present invention contains, with respect to the total weight of the composition, 0.01 to 10.0 wt. % of a Magnolia obovata bark extract, 0.01 to 10.0 wt. % of a Citrus unshiu peel extract, 0.01 to 10.0 wt. % of a wild soybean extract, 0.01 to 10.0 wt. % of a Ginkgo biloba leaf extract, and 0.01 to 10.0 wt. % of a Honeysuckle extract. The content of each ingredient less than 0.01 wt. % makes it impossible to provide a desired efficacy of the ingredient on the skin, while the content of each ingredient greater than 10.0 wt. % does not have any increase in the efficacy, reducing the efficiency of the ingredient and greatly deteriorating the usefulness of the formulation with a deteriorated worth as a cosmetic product.

The cosmetic composition for skin whitening according to the present invention contains a meladefying complex comprising a mixture of at least two selected from the group consisting of a Magnolia obovata bark extract, a Citrus unshiu peel extract, a wild soybean extract, a Ginkgo biloba leaf extract, and a Honeysuckle extract and uses the synergy effect of the active ingredients to provide a skin whitening effect significantly enhanced relative to the cosmetic composition using a single ingredient.

The composition of the present invention may further contain a known substance used for a skin whitening effect. For example, the composition may contain at least one selected from the group consisting of ascorbyl glucoside, licorice extract, arbutin, ascorbic acid, and kojic acid, which may be used in an amount of 0.5 to 5.0 wt. % with respect to the total weight of the composition. The content of the whitening substance less than 0.5 wt. % fails to provide an efficacy of the substance because the substance is ready to penetrate into the skin, while the content of the whitening substance greater than 5.0 wt. % makes the composition toxic or greatly increases the stickiness of the composition, deteriorating the worth of the composition as a cosmetic product.

The cosmetic composition of the present invention depresses and protects damaged melanocytes and makes the microscopic environment surrounding the melanocytes healthy to substantially inhibit a production of melanins and facilitate the removal of melanins, thereby providing a remarkable whitening effect; improves skin hyper-pigmentation and darkening of the skin tone; and reduces old keratin of the skin. Accordingly, the cosmetic composition of the present invention is effective as a whole skincare for treating skin spots like melasma or freckles and dark-toned skin.

The cosmetic composition of the present invention is not specifically limited in the type of formulation, which may include, for example, skin toner, emulsion lotion, massage cream, nutrition cream, facial mask pack, gel, or topical skin-cohesive cosmetics.

Hereinafter, the present invention will be described in further detail with reference to examples and experimental examples, which are not intended to limit the scope of the present invention.

PREPARATION EXAMPLE 1

Preparation of Magnolia Obovata Bark Extract

The bark from a Magnolia obovata tree washed with clean water was soaked in a solvent consisting of 70% purified water and 30% alcohol and kept at 25° C. for 6 hours to extract active ingredients. After extraction, the solution was subjected to one filtration with a 3 μm-pore filter and one filtration with a 1 μm-pore filter to eliminate foreign materials and then one filtration with a sterile filter to eliminate microorganisms to yield a Magnolia obovata bark extract.

PREPARATION EXAMPLE 2

Preparation of Citrus Unshiu Peel Extract

The citrus peel washed with clean water was soaked in a solvent consisting of 70% purified water and 30% alcohol and kept at 25° C. for 6 hours to extract active ingredients. After extraction, the solution was subjected to one filtration with a 3 μm-pore filter and one filtration with a 1 μm-pore filter to eliminate foreign materials and then one filtration with a sterile filter to eliminate microorganisms to yield a Citrus unshiu peel extract.

PREPARATION EXAMPLE 3

Preparation of Wild Soybean Extract

The wild soybeans washed with clean water were soaked in a solvent consisting of 70% purified water and 30% alcohol and kept at 25° C. for 6 hours to extract active ingredients. After extraction, the solution was subjected to one filtration with a 3 μm-pore filter and one filtration with a 1 μm-pore filter to eliminate foreign materials and then one filtration with a sterile filter to eliminate microorganisms to yield a wild soybean extract.

PREPARATION EXAMPLE 4

Preparation of *Ginkgo Biloba* Leaf Extract

The *Ginkgo biloba* leaves washed with clean water were soaked in a solvent consisting of 70% purified water and 30% alcohol and kept at 25° C. for 6 hours to extract active ingredients. After extraction, the solution was subjected to one filtration with a 3 μm-pore filter and one filtration with a 1 μm-pore filter to eliminate foreign materials and then one filtration with a sterile filter to eliminate microorganisms to yield a *Ginkgo biloba* leaf extract.

PREPARATION EXAMPLE 5

Preparation of Honeysuckle Extract

The Honeysuckle leaves and stems washed with clean water were soaked in a solvent consisting of 70% purified water and 30% alcohol and kept at 25° C. for 6 hours to extract active ingredients. After extraction, the solution was subjected to one filtration with a 3 μm-pore filter and one filtration with a 1 μm-pore filter to eliminate foreign materials and then one filtration with a sterile filter to eliminate microorganisms to yield a Honeysuckle extract.

EXAMPLES 1 TO 4 AND COMPARATIVE EXAMPLES 1 TO 6

For experiments regarding a whitening effect on the human skin, the cosmetic compositions of Examples 1 to 4 and Comparative Examples 1 to 6 were prepared according to the following table 1.

PREPARATION METHOD FOR EXAMPLES 1 TO 4 AND COMPARATIVE EXAMPLES 1 TO 6

(1) The ingredients 1 to 9 of Table 1 were blended together and dissolved to prepare an aqueous part.

(2) In a separate container, the ingredients 10 to 14 of Table 1 were dissolved at 50° C. to prepare an alcohol part.

(3) The alcohol part of the step (2) was added to the aqueous part of the step (1), and the mixture was stirred with an age-mixer.

(4) The mixture of the step (3) was removed of bubbles to prepare a cosmetic composition.

EXPERIMENTAL EXAMPLE 1

On 12 healthy men as subjects, an opaque tape with six 1.5 cm-diameter openings was applied on the upper arms of each subject. For each subject, skin darkening was induced under UV B radiation about 1.5 to 2 times the minimal erythema dose. Then, each of the compositions of Examples 1 to 4 and Comparative Examples 1 to 6 was applied to the respective openings twice a day (every morning and evening). After two months, the contrast of the skin was measured with a colorimeter.

To evaluate the whitening effect of each composition, the whiteness and darkness of the skin was measured with the colorimeter (e.g., Minolta CR 2002). It is general to use the L-a-b color system for this, and the present invention uses an "L" value to indicate the brightness of the skin in this test. For example, the natural skin of Korean people (without tanning) has an L value of 50 to 70. The L value was calibrated with a standard white boar, and the measurement was conducted repeatedly at least five times per each test area.

TABLE 1

| | Example | | | | Comparative Example | | | | | |
|---|---|---|---|---|---|---|---|---|---|---|
| Ingredient (wt. %) | 1 | 2 | 3 | 4 | 1 | 2 | 3 | 4 | 5 | 6 |
| 1. Purified water | To 100 | To 100 | To 100 | To 100 | To 100 | To 100 | To 100 | To 100 | To 100 | To 100 |
| 2. Dipropylene glycol | 5.0 | 5.0 | 5.0 | 5.0 | 5.0 | 5.0 | 5.0 | 5.0 | 5.0 | 5.0 |
| 3. Butylene glycol | 5.0 | 5.0 | 5.0 | 5.0 | 5.0 | 5.0 | 5.0 | 5.0 | 5.0 | 5.0 |
| 4. Bio-saccharide gum-1 | 4.0 | 4.0 | 4.0 | 4.0 | 4.0 | 4.0 | 4.0 | 4.0 | 4.0 | 4.0 |
| 5. *Magnolia obvota* bark extract (Prep. Example 1) | 1.0 | 1.0 | 1.0 | 1.0 | 5.0 | — | — | — | — | — |
| 6. Citrus unshiu peel extract (Prep. Example 2) | 1.0 | 1.0 | 1.0 | 1.0 | — | 5.0 | — | — | — | — |
| 7. Wild soybean extract (Prep. Example 3) | — | 1.0 | 1.0 | 1.0 | — | — | 5.0 | — | — | — |
| 8. *Ginko biloba* leaf extract (Prep. Example 4) | — | — | 1.0 | 1.0 | — | — | — | 5.0 | — | — |
| 9. Honeysuckle extract (Prep. Example 5) | — | — | — | 1.0 | — | — | — | — | 5.0 | — |
| 10. Ethanol | 5.0 | 5.0 | 5.0 | 5.0 | 5.0 | 5.0 | 5.0 | 5.0 | 5.0 | 5.0 |
| 11. Phenyl trimethicone | 0.2 | 0.2 | 0.2 | 0.2 | 0.2 | 0.2 | 0.2 | 0.2 | 0.2 | 0.2 |
| 12. Polyoxyethylene hydrogenated castor oil | 0.5 | 0.5 | 0.5 | 0.5 | 0.5 | 0.5 | 0.5 | 0.5 | 0.5 | 0.5 |
| 13. Preservatives | * | * | * | * | * | * | * | * | * | * |
| 14. Flavor | * | * | * | * | * | * | * | * | * | * |

Note)
*: Proper amount

The L value was gradually increased when test composition had a whitening effect. For a comparison of the test compositions, the difference ΔL in skin color between a start time point of application and an end time point of application was calculated according to the following equation 1. The results are presented in Table 2.

$$\Delta L = L \text{ value after 50 days of application} - L \text{ value upon application} \quad [\text{Equation 1}]$$

TABLE 2

Whitening Effect Test for Human Skin

| Test Composition | Whitening Effect (ΔL) |
| --- | --- |
| Example 1 | (2.79) |
| Example 2 | (3.15) |
| Example 3 | (3.46) |
| Example 4 | 3.89 |
| Comparative Example 1 | 2.42 |
| Comparative Example 2 | 2.04 |
| Comparative Example 3 | 1.27 |
| Comparative Example 4 | 1.15 |
| Comparative Example 5 | 1.98 |
| Comparative Example 6 | 0.67 |

As can be seen from Table 2, the compositions of Examples 1 to 4 containing at least two selected from the group consisting of a *Magnolia obovata* bark extract, a *Citrus unshiu* peel extract, a wild soybean extract, a *Ginkgo biloba* leaf extract, and a Honeysuckle extract were far superior in whitening effect due to the synergy effect of the active ingredients to the compositions of Comparative Examples 1 to 6 containing none of the active ingredients of the present invention or containing one of them alone.

Accordingly, the cosmetic compositions of the present invention depresses/protects damaged melanocytes and makes the microscopic environment surrounding the melanocytes to substantially inhibit the production of melanins and to facilitate melanin secretion, thereby achieving an excellent whitening effect.

EXPERIMENTAL EXAMPLE 2

Effect of Reducing Old Keratin

The cosmetic compositions for whitening effect according to Examples 1 to 4 and Comparative Examples 1 to 6 were evaluated in regard to the effect of reducing old keratin of the skin.

On 50 men and women without a skin disease as subjects, the cosmetic compositions of Examples 1 to 4 and Comparative Examples 1 to 6 were applied on the inner side of the forearm of each subject. After an elapse of 24 hours, the reduced amount of old keratin on the skin was measured using a Charm view (Moritex, Japan). The initial amount of old keratin on the skin was measured with the Charm view at a constant temperature (24° C.) and a constant humidity (40%) prior to application of the test substances and used as a reference value. The reduced amount of old keratin after 24 hours of the application was measured. The results are presented in Table 3.

TABLE 3

Variation (%) of Amount of Old Keratin according to Whitening Cosmetic Compositions

| Test Substance | Before Application | After 24 Hours |
| --- | --- | --- |
| Example 1 | (20.3) | (11.9) |
| Example 2 | (20.8) | (11.4) |
| Example 3 | (19.8) | (10.1) |
| Example 4 | 20.3 | 9.0 |
| Comparative Example 1 | 20.4 | 13.2 |
| Comparative Example 2 | 20.2 | 14.8 |
| Comparative Example 3 | 19.5 | 17.6 |
| Comparative Example 4 | 20.1 | 16.7 |
| Comparative Example 5 | 19.9 | 17.8 |
| Comparative Example 6 | 19.8 | 18.3 |

As can be seen from Table 3, the whitening cosmetic compositions of the present invention in Examples 1 to 4 were far superior in the effect of reducing old keratin of the skin to the compositions of Comparative Examples 1 to 6 containing none of the active ingredients of the present invention, that is, a *Magnolia obovata* bark extract, a *Citrus unshiu* peel extract, a wild soybean extract, a *Ginkgo biloba* leaf extract, and a Honeysuckle extract, or containing one of them alone.

Accordingly, due to the synergy effect of the active ingredients, such as a *Magnolia obovata* bark extract, a *Citrus unshiu* peel extract, a wild soybean extract, a *Ginkgo biloba* leaf extract, and a Honeysuckle extract, the compositions of the present invention effectively reduced the old keratin of the skin to provide even skin tone and make the skin healthy, shiny and clear.

EXPERIMENTAL EXAMPLE 3

Skin Safety Test

In order to evaluate the skin safety of the whitening cosmetic composition of the present invention, the compositions of Examples 1 to 4 were measured in regard to the skin irritation potency.

The measurement of the skin irritation potency was conducted in the dermatology department of Chungbuk University in South Korea. On 30 healthy adult people 33.2 years old on average as subjects, a closed patch containing each composition was applied to the back area of each subject and, after 48 hours, the skin response was observed within one hour after removal of the patch. The skin irritation potency was evaluated with reference to the CTFA guide line (1981) and the assessment standards of Frosch & Kligman, which are given in Table 4.

TABLE 4

| Skin Response | Score | Assessment Standards |
| --- | --- | --- |
| − | 0.0 | No change |
| + | 1.0 | Very slight erythema |
| ++ | 2.0 | Edges of area well-defined and slight erythema, edma and papule |
| +++ | 3.0 | Severe erythema, papule and bulla |
| ++++ | 4.0 | Very severe bulla |

All the 30 people with the patches containing the cosmetic compositions of the present invention according to Example 1 to 4 had an average skin irritation score of zero (0), which demonstrated that the cosmetic compositions caused no skin irritation. As the average skin irritation score below 1 indicates that the composition is very safe to the skin, the present is considered as a composition very excellent in skin safety.

What is claimed is:

1. A cosmetic composition for skin whitening comprising an amount of a mixture effective as a skin whitening active ingredient of a *Magnolia obovata* bark extract; a *Citrus unshiu* peel extract; and at least one herbal extract selected from the group consisting of a wild soybean extract, a *Ginkgo biloba* leaf extract, and a Honeysuckle extract.

2. The cosmetic composition for skin whitening as claimed in claim 1, wherein each of the *Magnolia obovata* bark extract, the *Citrus unshiu* peel extract, the wild soybean extract, the *Ginkgo biloba* leaf extract, and the Honeysuckle extract is used in an amount of 0.01 to 10 wt. % with respect to the total weight of the composition.

3. The cosmetic composition for skin whitening as claimed in claim 1, wherein the composition further comprises at least one selected from the group consisting of ascorbyl glucoside, licorice extract, arbutin, ascorbic acid, and kojic acid.

4. The cosmetic composition for skin whitening as claimed in claim 1, wherein the composition fundamentally inhibits production of melanin inside the skin or facilitates removal of melanin from the inside of the skin.

5. The cosmetic composition for skin whitening as claimed in claim 1, wherein the composition improves skin pigmentation and dark-toned skin.

6. The cosmetic composition for skin whitening as claimed in claim 1, wherein the composition reduces old keratin of the skin.

7. The cosmetic composition for skin whitening as claimed in claim 1, wherein each of the *Magnolia obovata* bark extract, the *Citrus unshiu* peel extract, the wild soybean extract, the *Ginkgo biloba* leaf extract, and the Honeysuckle extract is obtained by extracting with a solvent consisting of 70% water and 30% ethanol.

8. The cosmetic composition for skin whitening as claimed in claim 7, wherein extraction is carried out at 25° C.

9. The cosmetic composition for skin whitening as claimed in claim 1, wherein the Honeysuckle extract is an extract from a leaf and stem of Honeysuckle.

10. A method for whitening skin, comprising the step of topically applying to skin of a subject in need a cosmetic composition comprising an amount effective as a skin whitening active ingredient of a mixture of a *Magnolia obovata* bark extract; a *Citrus unshiu* peel extract; and at least one herbal extract selected from the group consisting of a wild soybean extract, a *Ginkgo biloba* leaf extract, and a Honeysuckle extract.

11. The method for whitening as claimed in claim 10, wherein each of the *Magnolia obovata* bark extract, the *Citrus unshiu* peel extract, the wild soybean extract, the *Ginkgo biloba* leaf extract, and the Honeysuckle extract is used in an amount of 0.01 to 10 wt. % with respect to the total weight of the composition.

12. The method for whitening as claimed in claim 10, wherein the composition further comprises at least one selected from the group consisting of ascorbyl glucoside, licorice extract, arbutin, ascorbic acid, and kojic acid.

13. The method for whitening as claimed in claim 10, wherein the composition fundamentally inhibits production of melanin inside the skin or facilitates removal of melanin from the inside of the skin.

14. The method for whitening as claimed in claim 10, wherein the composition improves skin pigmentation and dark-toned skin.

15. The method for whitening as claimed in claim 10, wherein the composition reduces old keratin of the skin.

* * * * *